United States Patent
Doorschodt

(10) Patent No.: US 7,635,341 B2
(45) Date of Patent: Dec. 22, 2009

(54) INSERTION SLEEVE ASSEMBLY

(75) Inventor: Benedict Marie Doorschodt, Amsterdam (NL)

(73) Assignee: Doorzand Trocar Protector B.V., Amsterdam (NL)

( * ) Notice: Subject to any disclaimer, the term of this patent is extended or adjusted under 35 U.S.C. 154(b) by 275 days.

(21) Appl. No.: 10/557,286

(22) PCT Filed: May 19, 2004

(86) PCT No.: PCT/NL2004/000353

§ 371 (c)(1),
(2), (4) Date: Aug. 24, 2007

(87) PCT Pub. No.: WO2004/100797

PCT Pub. Date: Nov. 25, 2004

(65) Prior Publication Data

US 2008/0051675 A1    Feb. 28, 2008

(30) Foreign Application Priority Data

May 19, 2003    (NL)    .................................... 1023462

(51) Int. Cl.
*A61B 5/00*    (2006.01)
*A61B 10/00*    (2006.01)
(52) U.S. Cl. ...................... 600/585; 600/562
(58) Field of Classification Search ......... 600/562–567, 600/585; 424/422, 423, 449, 486; 604/523
See application file for complete search history.

(56) References Cited

U.S. PATENT DOCUMENTS

| 4,838,280 | A | 6/1989 | Haaga |
| 5,976,146 | A | 11/1999 | Ogawa et al. |
| 6,884,427 | B1 * | 4/2005 | Barrows ..................... 424/422 |
| 2003/0050664 | A1 | 3/2003 | Solem |
| 2003/0097079 | A1 * | 5/2003 | Garcia ........................ 600/567 |

FOREIGN PATENT DOCUMENTS

| CN | 1146466 A | 4/1997 |
| EP | 1 070 514 | 1/2001 |
| NL | 9302140 | 7/1995 |

\* cited by examiner

*Primary Examiner*—Max Hindenburg
*Assistant Examiner*—Brian Szmal
(74) *Attorney, Agent, or Firm*—The Webb Law Firm

(57) ABSTRACT

An insertion sleeve assembly consisting of a sleeve and an insertion instrument. The sleeve is made of a material that collapses after having been introduced into the body and on withdrawal of the biopsy needle. Cells are captured as a result. Such a material can be a material that is relatively rigid at relatively low temperature and low humidity outside the body and becomes soft on insertion into the body under the influence of temperature and moisture. The insertion sleeve can be provided with a number of break locations so that no stress can arise between the various parts of the body after withdrawal of the biopsy needle.

13 Claims, 3 Drawing Sheets

INSERTION SLEEVE ASSEMBLY

The present invention relates to an insertion sleeve assembly comprising an insertion instrument for performing a medical operation and a sleeve of bio-absorbable material guiding said instrument.

Such an assembly is disclosed in Netherlands Patent Application 9302140. In this application an insertion sleeve assembly is described with reference to a biopsy needle assembly. Here the insertion instrument is the biopsy needle and after a sample has been taken this biopsy needle is withdrawn and the sleeve remains behind. Because of the bio-absorbable nature thereof, this will disappear by itself after some time.

However, it has been found that when the biopsy needle is withdrawn cells from the possibly infected tissue are spread along the inside of the sleeve by the biopsy needle as it is withdrawn. The insertion sleeve must have a certain rigidity in order to be able to be introduced into the body together with the biopsy needle. As a result of the same rigidity, the sleeve remains intact for some time after the needle has been withdrawn until it dissolves. If the sleeve were to be made of a softer material, fitting it on the biopsy needle would not be possible without it rolling up and the like.

It has been found that the risk of infection remains while the sleeve is intact and that the risk of dissemination of undesirable cell material from inside the body into the skin is real.

The aim of the present invention is to avoid this disadvantage.

This aim is realised with an insertion sleeve assembly as described above in that said sleeve is made of a material that is relatively rigid outside the body and becomes softer after introduction into the body and collapses onto itself when the instrument is withdrawn.

According to the present invention the sleeve is made such that this is, on the one hand, sufficiently rigid to be able to be introduced into the body together with the biopsy needle without rolling up and, on the other hand, is sufficiently soft to collapse after the biopsy needle has been removed. Consequently it is possible, for example, for tumour cells to be captured by the sleeve when a biopsy needle is withdrawn. Optionally, the sleeve can close off completely when it collapses.

Such characteristics can be obtained in many ways known in the state of the art.

According to an advantageous embodiment of the invention, the sleeve is made of a material that is relatively rigid at temperatures below 30° C. and in an environment free from moisture. However, when the temperature is raised in combination with a high moisture content, such as when the sleeve is inserted in the human body, the material that is used according to a preferred embodiment will rapidly become soft, as a result of which the sleeve will not remain in place without the support of the biopsy needle. This means that with this material relatively rapid insertion of the sleeve in combination with a needle is possible without the risk of rolling up, but that, on the other hand, the sleeve collapses immediately when a needle is withdrawn.

Many materials have the characteristics described above. A few examples thereof are poly-ε-caprolactone-DL-lactide copolymer; ε-caprolactone; D-lactide; L-lactide; DL-lactide and poly(DL-lactide-co-glycolide).

Particularly good results are obtained with a material consisting of a combination of polyglycolide (30-50% (m/m)), polylactic acid (25-50% (m/m)) and caprolactone (4-25% (m/m)).

According to an advantageous embodiment of the invention, the material of the sleeve is made such that the outside thereof has staunching properties. As a result, the effect of a haemorrhage can be prevented. Good adhesion between the exterior of the sleeve and the surrounding tissue is provided by absorbing properties.

Furthermore, it has been found that when a sleeve is inserted through various organs appreciable stresses are exerted on the human body in the period before said sleeve dissolves completely. After all, various parts of the human body move relative to one another. Organs that are in the abdominal cavity are one example. The sleeve still has an appreciable strength immediately after the insertion instrument has been removed or, alternatively, immediately after fitting the sleeve, so that in the case of such a movement of parts of the human body relative to one another stresses can arise that are undesirable and can lead to damage to the organs but also to undesired displacement of the sleeve.

This applies in particular if there is a tumour close to the end of the sleeve, there being a risk of metastases as a result of displacement of the sleeve.

A further aim of the present invention is to overcome this disadvantage and to provide an insertion sleeve assembly that can be used safely.

This further aim is realised with an insertion sleeve as described above in that said sleeve is provided with at least two break locations, the minimal distance from the distal break point to the distal end being 15 mm and the distance between said break locations being less than 20 mm.

As a result of providing the break locations, breaks will occur when a minimum stress is exceeded, which minimum stress, of course, is so chosen that no damage whatsoever to the organs takes place or, alternatively, no movement whatsoever of the sleeve is caused under this stress. This break has no further consequence whatsoever, but prevents further stress. The break locations or points are provided such that the break takes place outside the organ in which the medical intervention has been carried out. That is to say, the minimum distance described above is essential for proper functioning thereof. After all, the stresses mentioned above will not arise in the organ concerned, for example breast or prostate, and it is not desirable that the sleeve breaks in the organ, as a result of which part of the sleeve moves out of the organ with all the harmful associated consequences, such as infection.

It is pointed out that an insertion sleeve provided with a break point or location close to the end thereof is disclosed in U.S. Pat. No. 4,838,280. The aim of the structure described in the U.S. patent is precisely to allow a break to occur within the organ concerned.

As insertion instrument is understood to be any medical instrument that can be used in combination with a sleeve. Apart from the biopsy needle described above, a wide variety of instruments that are used for so-called exploratory surgery fall under this definition.

According to an advantageous variant of the invention, there are at least five break locations or points.

The sleeve can be made in any way in order to function in an optimum manner. For instance, it is possible to make this from a single material that is provided with thinner regions in order to create the break locations.

It is furthermore possible to build up the sleeve from a number of layers of material. In particular, it is possible to produce this from a relatively weak material and to provide it with reinforcing rings. On the one hand, adequate strength and, on the other hand, adequate flexibility are achieved by the use of these rings. These rings can be circular rings, but can also be made as a continuous spiral.

It must be understood that the characteristics described above with regard to the sleeve being breakable can also be employed with a sleeve made of another material, that is to say a material that is soft and/or rigid under all conditions.

Moreover, the sleeve can be so made that this has particular properties. Examples thereof are, apart from being bio-absorbable, the use of material with a blood-staunching effect and material that counteracts infection. Materials used for the sleeve can be polyglucolactate, caprolactone, polyglycolide and combinations thereof According to a further advantageous embodiment of the invention, the distance between the break locations is 3-7 mm.

The sleeve has a wall thickness of preferably between 0.5 and 1.5 mm.

The invention will be explained in more detail below with reference to an illustrative embodiment shown in the drawing. In the drawing.

Figure 2:
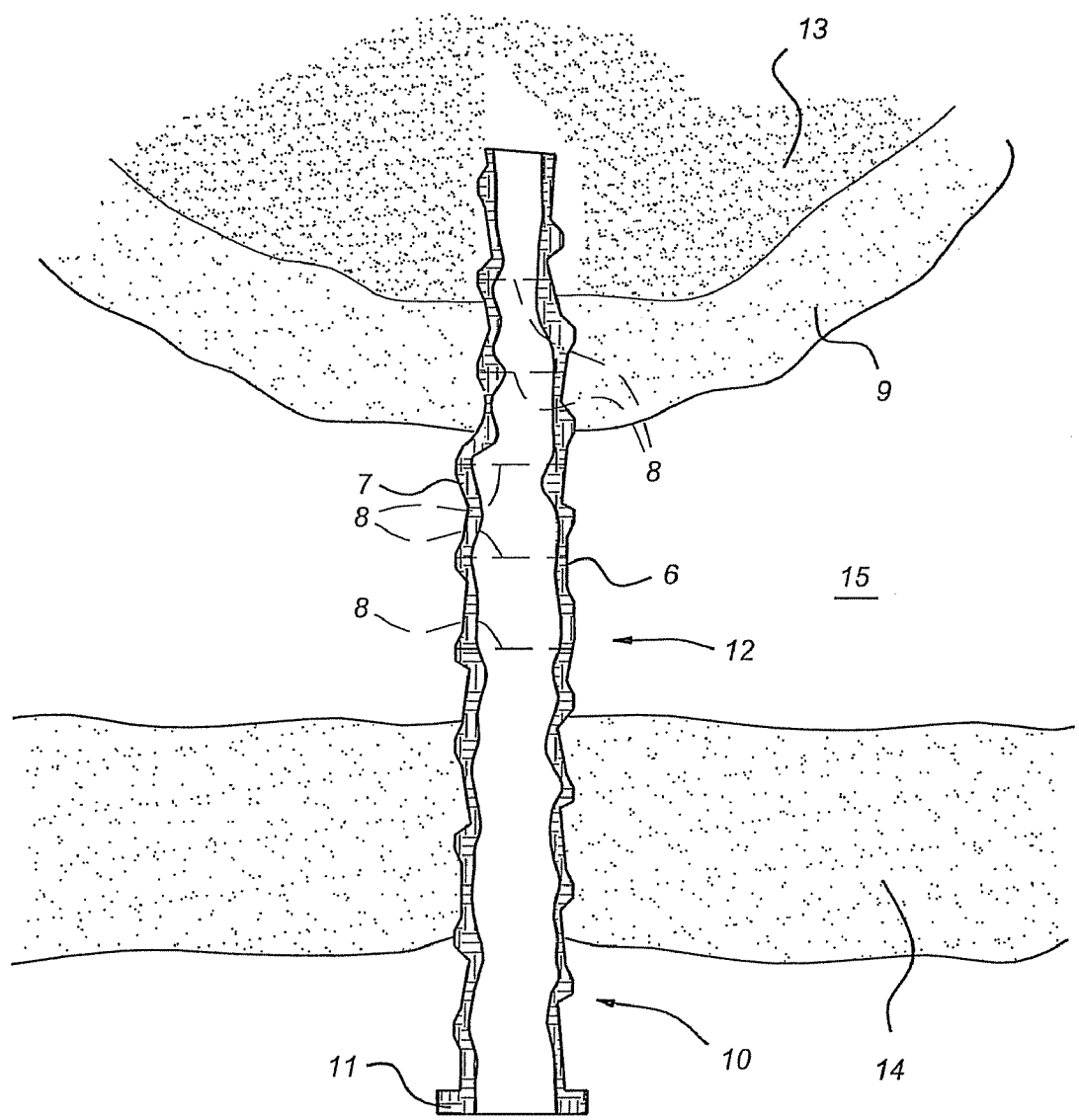
FIG. 2 shows the construction according to FIG. 1 immediately after removal of the biopsy needle.

In the drawing an insertion sleeve assembly is shown by 10. This consists of a sleeve 12 and an instrument, such as a biopsy needle 3, to be inserted therein. Sleeve 12 is provided with a stop 11. Sleeve 12 is introduced together with needle 13 into the body in order to take a sample of section 13 of organ 9. Sleeve 12 provides permanent protection in order to prevent infection or other undesired reactions on withdrawal of needle 3. After the removal of needle 3, the sleeve will (partially) collapse (FIG. 2). Because this sleeve is made of bio-absorbable material, such as polyglucolactate or caprolactone or a combination thereof, the sleeve 12 will disappear after some time has elapsed.

Figure 1:
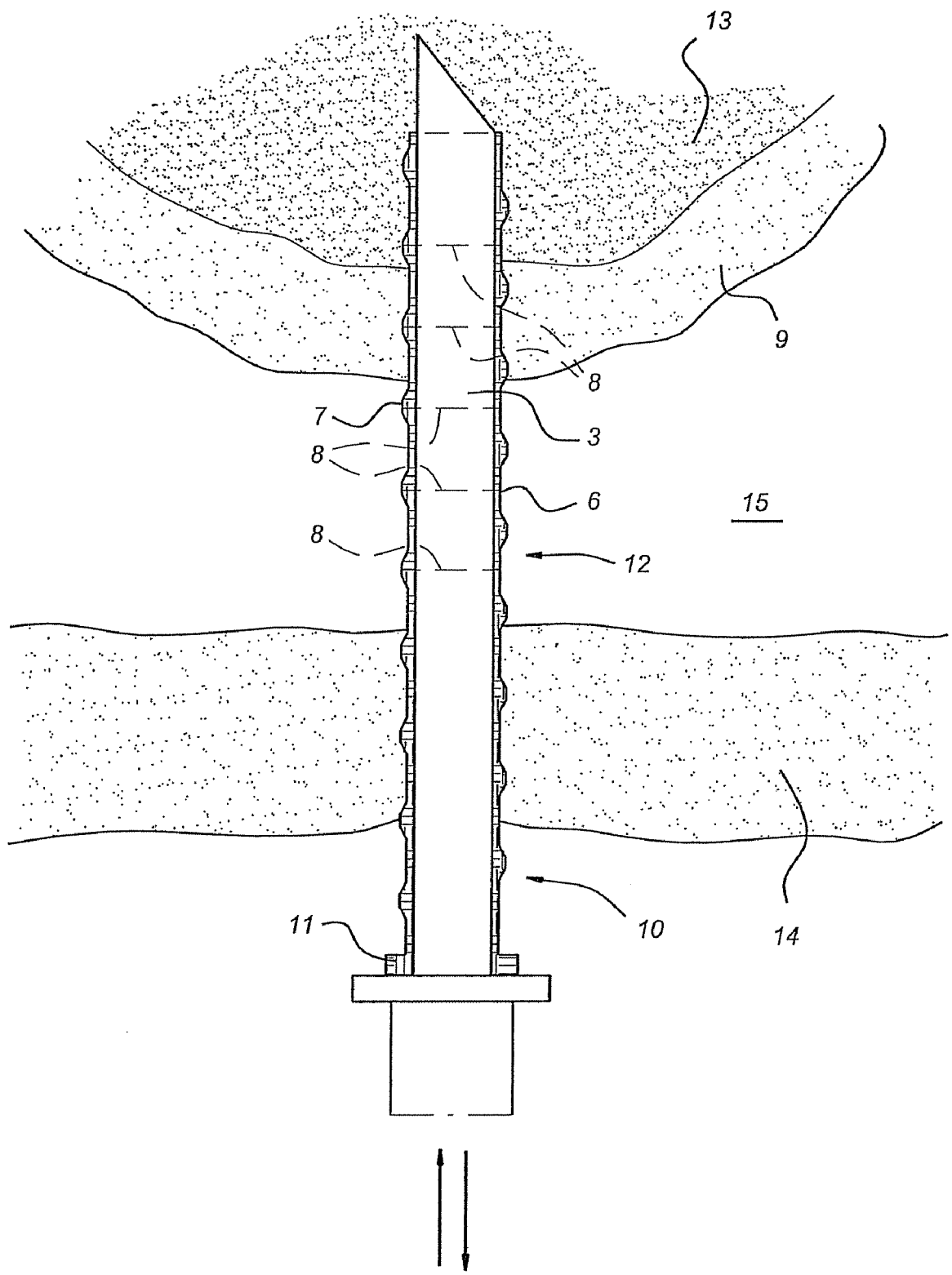
FIG. 1 shows the insertion sleeve assembly according to the present invention constructed as a biopsy needle assembly.

As can be seen from FIGS. 1 and 2, the sleeve 12 has a number of break points extending all round, which are indicated by 8. The mutual spacing between the break points 8 is approximately 5 cm. The sleeve is made up of a layer of film material 6 reinforced by a spiral 7.

Figure 3:
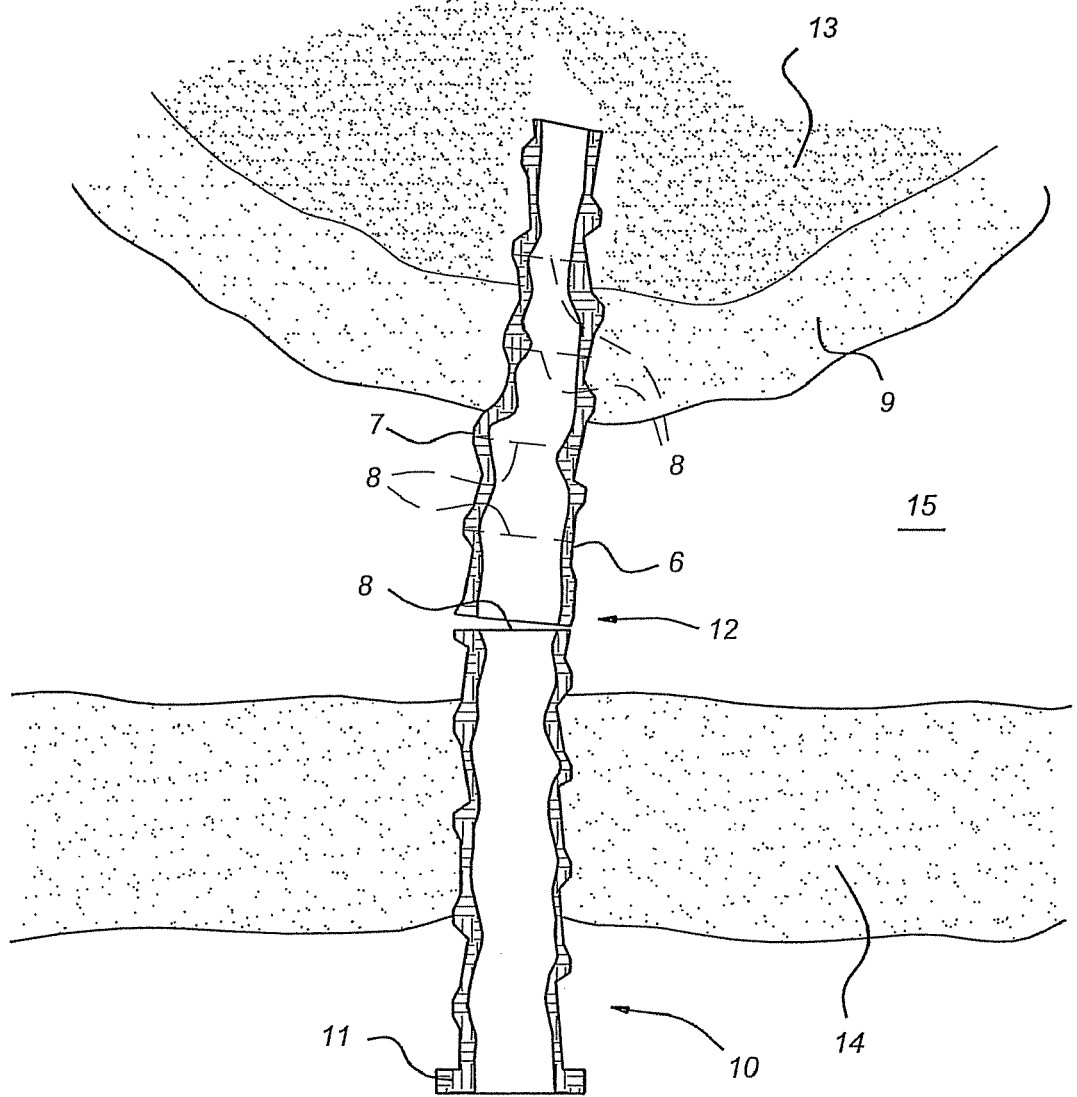
FIG. 3 shows the construction according to FIG. 2 after break has taken place.

The situation after insertion of the assembly and when taking the sample in organ 13 is shown in FIG. 1. The sleeve 12 is relatively rigid when it is inserted. As a result, it can be introduced at the same time as the needle 3 without the risk of rolling up. The situation after the removal of biopsy needle 3 is shown in FIG. 2. Here the sleeve remains in the body. The material of the sleeve will become soft as a result of absorbing moisture from the surrounding body tissue and the rising temperature, as a result of which, as shown, the sleeve collapses and possibly sticks to itself internally. A somewhat flexible connection between organ 9, cavity 15 and skin 14 is produced by the flexible film 6 and the rings or spiral 7. By this means it is possible for small mutual movements to be absorbed. However, if these movements become too large, a tensile or compressive stress will be produced between organ 9 and other parts of the human body. Were the sleeve not to break, there is the risk that some organs are displaced and this displacement is sometimes not reversed by itself. The break points 8 act to prevent this excessive stress and thus damage. These break locations provide for breakage of the various parts of sleeve 12. One example of such a break is shown in FIG. 3. It must be understood that as a result of the relatively rigid solid nature of organ 9, break will always occur outside this organ, such as, for example, in the cavity 15. In general, break will occur at the interface between the organ 13 and cavity 15 or, alternatively, between cavity 15 and skin 14. It will be understood that movement between organs can also occur in other parts of the human body and break will then occur at the transition between two organs where mutual movement takes place.

Although the invention has been described above with reference to a preferred embodiment, it will be understood by those skilled in the art that numerous modifications can be made thereto without going beyond the scope of the present invention as described in the appended claims.

The invention claimed is:

1. An insertion sleeve assembly comprising an insertion instrument for performing a medical operation and a sleeve of bio-absorbable material defining an interior for guiding said instrument, said sleeve having an opening and comprising a stop adjacent the opening, said sleeve being made of a material that is relatively rigid outside the body and becomes softer after introduction into the body and collapses inwardly when the instrument is withdrawn, wherein said stop is configured to abut against an area of patient's skin surrounding an insertion site so as to prevent skin contamination.

2. The insertion sleeve assembly according to claim 1, wherein said sleeve is made of a material that is relatively rigid at temperatures below 30° C. and not in contact with water.

3. The insertion sleeve assembly according to claim 1, wherein said material comprises a material from the group comprising: polyglycolide; poly-ϵ-caprolactone-DL-lactide copolymer; ϵ-caprolactone; D-lactide; L-lactide; DL-lactide and poly(DL-lactide-co-glycolide).

4. The insertion sleeve assembly according to claim 1, wherein said material comprises a combination of polyglycolide (30-50% by wt), polylactic acid (25-50% by wt) and caprolactone (4-25% by wt).

5. The insertion sleeve assembly according to claim 1, wherein said sleeve has blood-staunching properties on the outside.

6. The insertion sleeve assembly according to claim 1, wherein said sleeve is provided with at least two break points, the minimal distance from the distal break point to the distal end being 15 mm and the distance between said break points being less than 20 mm.

7. The insertion sleeve assembly according to claim 6, wherein said sleeve is designed for direct contact with said insertion instrument and the body.

8. The insertion sleeve assembly according to claim 6, wherein said sleeve comprises a continuous base sleeve of flexible material and a number of rings arranged around the continuous base sleeve.

9. The insertion sleeve assembly according to claim 8, wherein said sleeve has a wall thickness of 0.5-1.5 mm.

10. The insertion sleeve assembly according to claim 8, wherein said sleeve is made of a blood-staunching material.

11. The insertion sleeve assembly according to claim 1, wherein the sleeve is made of a bio-absorbable material.

12. An insertion sleeve assembly comprising an insertion instrument for performing a medical operation and a sleeve of bio-absorbable material guiding said instrument, said sleeve being made of a material that is relatively rigid outside the body and becomes softer after introduction into the body and collapses inwardly when the instrument is withdrawn, wherein said sleeve has at least five break locations, the minimal distance from the distal break location to the distal end being 15 mm and the distance between said break locations being less than 20 mm.

13. An insertion sleeve assembly comprising an insertion instrument for performing a medical operation and a sleeve of bio-absorbable material defining an interior for guiding said instrument, said sleeve having an opening and comprising a stop adjacent the opening, said sleeve being made of a material that is relatively rigid outside the body and becomes softer after introduction into the body and collapses inwardly when the instrument is withdrawn,
    wherein said sleeve is provided with at least two break points, the minimal distance from the distal break point to the distal end being 15 mm,
    wherein said sleeve is designed for direct contact with said insertion instrument and the body, and
    wherein the distance between said break points is 3-7 mm.

* * * * *